US010436158B2

(12) United States Patent
Ito

(10) Patent No.: US 10,436,158 B2
(45) Date of Patent: Oct. 8, 2019

(54) ABNORMALITY DETECTION DEVICE FOR HUMIDITY SENSOR

(71) Applicant: TOYOTA JIDOSHA KABUSHIKI KAISHA, Toyota-shi, Aichi-ken (JP)

(72) Inventor: Hironori Ito, Susono (JP)

(73) Assignee: TOYOTA JIDOSHA KABUSHIKI KAISHA, Toyota-shi (JP)

( * ) Notice: Subject to any disclaimer, the term of this patent is extended or adjusted under 35 U.S.C. 154(b) by 229 days.

(21) Appl. No.: 15/350,565

(22) Filed: Nov. 14, 2016

(65) Prior Publication Data

US 2017/0198666 A1 Jul. 13, 2017

(30) Foreign Application Priority Data

Jan. 13, 2016 (JP) ................................. 2016-004525

(51) Int. Cl.
*F02M 35/10* (2006.01)
*F02D 41/22* (2006.01)
*G01N 25/56* (2006.01)

(52) U.S. Cl.
CPC ..... *F02M 35/10393* (2013.01); *F02D 41/222* (2013.01); *F02M 35/1038* (2013.01); *G01N 25/56* (2013.01); *F02D 2200/0414* (2013.01); *F02D 2200/0418* (2013.01); *Y02T 10/40* (2013.01)

(58) Field of Classification Search
CPC .......... F02M 35/10393; F02M 35/1038; F02D 41/222; F02D 2200/0418; F02D 2200/0414; G01N 25/56; Y02T 10/40
See application file for complete search history.

(56) References Cited

U.S. PATENT DOCUMENTS 9,224,252 B1* 12/2015 Guo ..................... G07C 5/0808
2002/0053199 A1* 5/2002 Sato ...................... F01N 3/0835
60/277

(Continued)

FOREIGN PATENT DOCUMENTS

JP 2002-048010 A 2/2002
JP 2003-148135 A 5/2003

(Continued)

*Primary Examiner* — Stephanie E Bloss
*Assistant Examiner* — Mohammad K Islam
(74) *Attorney, Agent, or Firm* — Hunton Andrews Kurth LLP

(57) ABSTRACT

An abnormality detection device for a humidity sensor has a humidity sensor disposed in an intake passage, a temperature sensor to detect an intake air temperature, and a controller. The controller is configured to detect a first sensor signal at a time of the intake air temperature being a first intake air temperature, and a second sensor signal at a time of the intake air temperature changing from the first intake air temperature and reaching a second intake air temperature, calculate values from which an influence of a temperature difference between the first and second intake air temperatures is excluded, from the first sensor signal and the second sensor signal, as respective humidity index values, and detect presence or absence of abnormality of the humidity sensor according to whether or not a deviation degree of these humidity index values is larger than a predetermined degree.

12 Claims, 7 Drawing Sheets

(56) References Cited

U.S. PATENT DOCUMENTS

| | | | |
|---|---|---|---|
| 2002/0053343 A1* | 5/2002 | Sato | F02M 26/46 123/568.16 |
| 2002/0078733 A1* | 6/2002 | Seakins | G01N 27/223 73/29.02 |
| 2003/0011466 A1* | 1/2003 | Samuel | A45C 13/24 340/5.73 |
| 2003/0046979 A1* | 3/2003 | Yamazaki | F01N 3/0835 73/29.02 |
| 2003/0106304 A1 | 6/2003 | Miyahara et al. | |
| 2004/0237646 A1* | 12/2004 | Fujita | G01N 27/121 73/335.05 |
| 2005/0072411 A1* | 4/2005 | Cullen | F02D 41/021 123/690 |
| 2008/0315000 A1* | 12/2008 | Gorthala | B60H 1/00785 236/46 C |
| 2009/0254245 A1* | 10/2009 | Bauerle | F02D 41/222 701/29.2 |
| 2009/0297184 A1* | 12/2009 | Kubo | G01N 27/121 399/44 |
| 2011/0063122 A1* | 3/2011 | Matsubara | G05B 19/406 340/679 |
| 2011/0191064 A1* | 8/2011 | Fukai | G01D 21/00 702/183 |
| 2011/0254554 A1* | 10/2011 | Harbers | H05B 33/0893 324/414 |
| 2012/0227719 A1* | 9/2012 | Surnilla | F02D 41/0245 123/676 |
| 2012/0253691 A1* | 10/2012 | Graf | G01N 27/223 702/24 |
| 2014/0105621 A1* | 4/2014 | Imanaka | G03G 15/0266 399/26 |
| 2014/0238348 A1* | 8/2014 | Pursifull | F02M 25/0221 123/434 |
| 2014/0238369 A1* | 8/2014 | Jankovic | F02D 41/144 123/690 |
| 2014/0238370 A1* | 8/2014 | Pursifull | F02D 41/005 123/690 |
| 2014/0253735 A1* | 9/2014 | Fox | H04N 5/2252 348/164 |
| 2014/0298880 A1* | 10/2014 | Pursifull | G01N 33/0006 73/1.06 |
| 2014/0316676 A1* | 10/2014 | Pursifull | F02P 5/045 701/103 |
| 2015/0124850 A1* | 5/2015 | Parthasarathy | G01N 25/72 374/4 |
| 2016/0161313 A1* | 6/2016 | Yamaguchi | G01F 1/684 73/114.34 |
| 2016/0202200 A1* | 7/2016 | Nakano | G01N 27/18 73/23.31 |
| 2017/0016415 A1* | 1/2017 | Hoshika | G01N 27/223 |
| 2017/0059381 A1* | 3/2017 | Ban | G01F 1/696 |
| 2017/0082051 A1* | 3/2017 | Hoshika | F02D 41/18 |
| 2017/0205261 A1* | 7/2017 | Yogo | G01F 1/50 |
| 2017/0268442 A1* | 9/2017 | Oryoji | F02D 45/00 |

FOREIGN PATENT DOCUMENTS

| | | |
|---|---|---|
| JP | 2003-172192 A | 6/2003 |
| JP | 2010-223179 A | 10/2010 |
| JP | 2010-237128 A | 10/2010 |

* cited by examiner

ABNORMALITY DETECTION DEVICE FOR HUMIDITY SENSOR

CROSS-REFERENCE TO RELATED APPLICATION

The present application claims priority to Japanese Patent Application No. 2016-004525 filed on Jan. 13, 2016, which is incorporated herein by reference in its entirety.

TECHNICAL FIELD

Embodiments of the present invention relates to an abnormality detection device for a humidity sensor, and more particularly relates to a device that detects presence or absence of abnormality in a humidity sensor disposed in an intake passage of an internal combustion engine.

BACKGROUND

Conventionally, there has been disclosed a device that detects presence or absence of a malfunction of a humidity sensor provided in an exhaust system of an internal combustion engine, for example, in Patent Literature 1. In this device, the humidity sensor is provided in the vicinity of a hydrocarbon adsorbent provided in an exhaust system. When the operation of the internal combustion engine is stopped, water in the exhaust gas remaining around the hydrocarbon adsorbent adsorbs to the hydrocarbon adsorbent. Subsequently, when the hydrocarbon adsorbent is saturated with the adsorbing water, the humidity in the vicinity of the hydrocarbon adsorbent becomes a substantially constant humidity. At this time, if the humidity sensor is normal, the humidity stays within a certain range. The device of Patent Literature 1 detects presence or absence of a malfunction of the humidity sensor by the output of the humidity sensor at the time of the output of the humidity sensor becoming substantially constant after the operation of the internal combustion engine is stopped, by using the above phenomenon.

Following is a list of patent literatures which the applicant has noticed as related arts of embodiments the present invention.

Patent Literature 1: JP 2003-172192 A
Patent Literature 2: JP 2010-223179 A
Patent Literature 3: JP 2003-148135 A
Patent Literature 4: JP 2002-048010 A

SUMMARY

Incidentally, Patent Literature 2, for example, discloses a device in which a humidity sensor is disposed in an intake passage of an internal combustion engine. The output of a humidity sensor is used in control of an internal combustion engine, and therefore, when a malfunction occurs to the humidity sensor, the occurrence of the malfunction is desirably detected quickly. In this regard, the malfunction detection technique of Patent Literature 1 described above detects presence or absence of the malfunction of the humidity sensor by using a change in the humidity in exhaust gas, and therefore, cannot be applied to detection of abnormality of the humidity sensor disposed in an intake passage. Consequently, it has been desired to construct a device for detecting presence or absence of abnormality of the humidity sensor disposed in the intake passage of an internal combustion engine onboard.

The present invention is devised to solve the problem as described above, and has an object to provide an abnormality detection device for a humidity sensor capable of detecting presence or absence of abnormality of the humidity sensor disposed in an intake passage of an internal combustion engine with high precision.

In order to achieve the above described object, a first embodiment of the present invention is an abnormality detection device for a humidity sensor comprising:

a humidity sensor that is disposed in an intake passage of an internal combustion engine, and outputs a sensor signal corresponding to relative humidity of intake air in the intake passage;

a temperature sensor to detect an intake air temperature that is a temperature of the intake air; and a processing circuitry that is configured to detect presence or absence of abnormality of the humidity sensor based on the sensor signal and the intake air temperature, wherein the processing circuitry is configured to:

detect a first sensor signal that is the sensor signal at a time of the intake air temperature being a first intake air temperature, and a second sensor signal that is the sensor signal at a time of the intake air temperature changing from the first intake air temperature and reaching a second intake air temperature, calculate values from which an influence of a temperature difference between the first intake air temperature and the second intake air temperature is excluded, from the first sensor signal and the second sensor signal, as a first humidity index value and a second humidity index value, respectively, and detect presence or absence of abnormality of the humidity sensor according to whether or not a deviation degree of the first humidity index value and the second humidity index value is larger than a predetermined degree.

A second embodiment of the present invention is the abnormality detection device for a humidity sensor according to the first embodiment, wherein the processing circuitry is configured to:

calculate a value correlated with the relative humidity at a time of the intake air temperature being a predetermined reference intake air temperature, as the first humidity index value, by using the first sensor signal; and calculate a value correlated with the relative humidity at a time of the intake air temperature being the reference intake air temperature, as the second humidity index value, by using the second sensor signal.

A third embodiment of the present invention is the abnormality detection device for a humidity sensor according to the second embodiment, wherein the reference intake air temperature is the second intake air temperature.

A fourth embodiment of the present invention is the abnormality detection device for a humidity sensor according to the second embodiment, wherein the reference intake air temperature is the first intake air temperature.

A fifth embodiment of the present invention is the abnormality detection device for a humidity sensor according to the first embodiment, wherein the processing circuitry is configured to:

calculate a value correlated with first absolute humidity that is absolute humidity at the time of the intake air temperature being the first intake air temperature, as the first humidity index value, by using the first sensor signal, and calculate a value correlated with second absolute humidity that is absolute humidity at a time of the intake air temperature being the second intake air temperature, as the second humidity index value, by using the second sensor signal.

A sixth embodiment of the present invention is the abnormality detection device for a humidity sensor according to the first embodiment, wherein the processing circuitry is configured to detect the first sensor signal and the second sensor signal when the intake air temperature changes from the first intake air temperature to the second intake air temperature, in a warming-up period or a soak period of the internal combustion engine.

A seventh embodiment of the present invention is the abnormality detection device for a humidity sensor according to the first embodiment, wherein the processing circuitry is configured to restrict detection of the first sensor signal and the second sensor signal, until an integrated value of a volume of intake air that is taken into the intake passage after start of the internal combustion engine exceeds a capacity from an inlet to the humidity sensor in the intake passage, in a warming-up period of the internal combustion engine.

A eighth embodiment of the present invention is the abnormality detection device for a humidity sensor according to the first embodiment, wherein the processing circuitry is configured to set the second intake air temperature in such a manner that the temperature difference becomes a predetermined temperature difference or more.

A ninth embodiment of the present invention is the abnormality detection device for a humidity sensor according to the first embodiment, wherein the processing circuitry is configured to restrict detection of the first sensor signal and the second sensor signal when gas containing fuel components flows in the intake passage of the internal combustion engine.

Since the humidity sensor outputs the sensor signal corresponding to the relative humidity, the detected sensor signal changes in accordance with the temperature of the intake air at that time. According to the first embodiment of the present invention, the influence of the temperature difference between the first intake air temperature and the second intake air temperature is excluded from the first sensor signal at the time of the first intake air temperature, and the second sensor signal at the time of the intake air temperature changing from the first intake air temperature and reaching the second intake air temperature. Consequently, according to this embodiment, the two sensor signals with different intake air temperatures can be compared after the influence of the temperature difference is excluded, and therefore it becomes possible to detect presence or absence of abnormality of the humidity sensor with high precision.

According to the second embodiment of the present invention, the values which are correlated with the relative humidity in the case of the reference intake air temperature are respectively calculated from the two sensor signals with different intake air temperatures. Consequently, according to this embodiment, the influence of the temperature difference between the first intake air temperature and the second intake air temperature can be excluded from the first sensor signal and the second sensor signal.

According to the third embodiment of the present invention, the relative humidity in the case where the intake air temperature changes to the second intake air temperature is calculated by using the first sensor signal in the case of the first intake air temperature. Consequently, according to this embodiment, the influence of the temperature difference between the first intake air temperature and the second intake air temperature can be excluded from the first sensor signal and the second sensor signal.

According to the fourth embodiment of the present invention, the relative humidity in the case where the intake air temperature changes to the first intake air temperature is calculated by using the second sensor signal in the case of the second intake air temperature. Consequently, according to this embodiment, the influence of the temperature difference between the first intake air temperature and the second intake air temperature can be excluded from the first sensor signal and the second sensor signal.

According to the fifth embodiment of the present invention, the values which are correlated with the absolute humidity are calculated from the respective sensor signals, as the values from which the influence of the temperature difference between the first intake air temperature and the second intake air temperature is excluded, from the first sensor signal and the second sensor signal. Since the absolute humidity is the value that does not depend on the temperature, the influence of the temperature difference between the first intake air temperature and the second intake air temperature can be excluded from the first sensor signal and the second sensor signal.

In the warming-up period of the internal combustion engine, the intake air temperature rises. Further, in the soak period of the internal combustion engine, the intake air temperature lowers. Consequently, according to the sixth embodiment of the present invention, presence or absence of abnormality of the humidity sensor can be detected by using the change of the ambient temperature of the humidity sensor in the warming-up period and the soak period of the internal combustion engine.

It is conceivable that in the intake air passage before start of the internal combustion engine, the humidity is different from the humidity of external air. According to the seventh embodiment of the present invention, the sensor signal before the external air which is taken in after start of the internal combustion engine reaches the humidity sensor can be prevented from being used, and therefore it becomes possible to restrain error detection of abnormality of the humidity sensor.

According to the eighth embodiment of the present invention, the sensor signal in the case where the temperature difference between the first intake air temperature and the second intake air temperature is smaller than the predetermined temperature difference can be prevented from being used, and therefore it becomes possible to restrain error detection of abnormality of the humidity sensor.

According to the ninth embodiment of the present invention, the sensor signal in the case where gas containing fuel components flows in the intake passage can be prevented from being used, and therefore it becomes possible to restrain error detection of abnormality of the humidity sensor by using the sensor signal of the air different from external air.

DESCRIPTION OF EMBODIMENTS

First Embodiment

Hereinafter, a first embodiment of the present invention will be described with reference to the drawings.

1-1. System Configuration of the First Embodiment of the Present Invention

Figure 1:
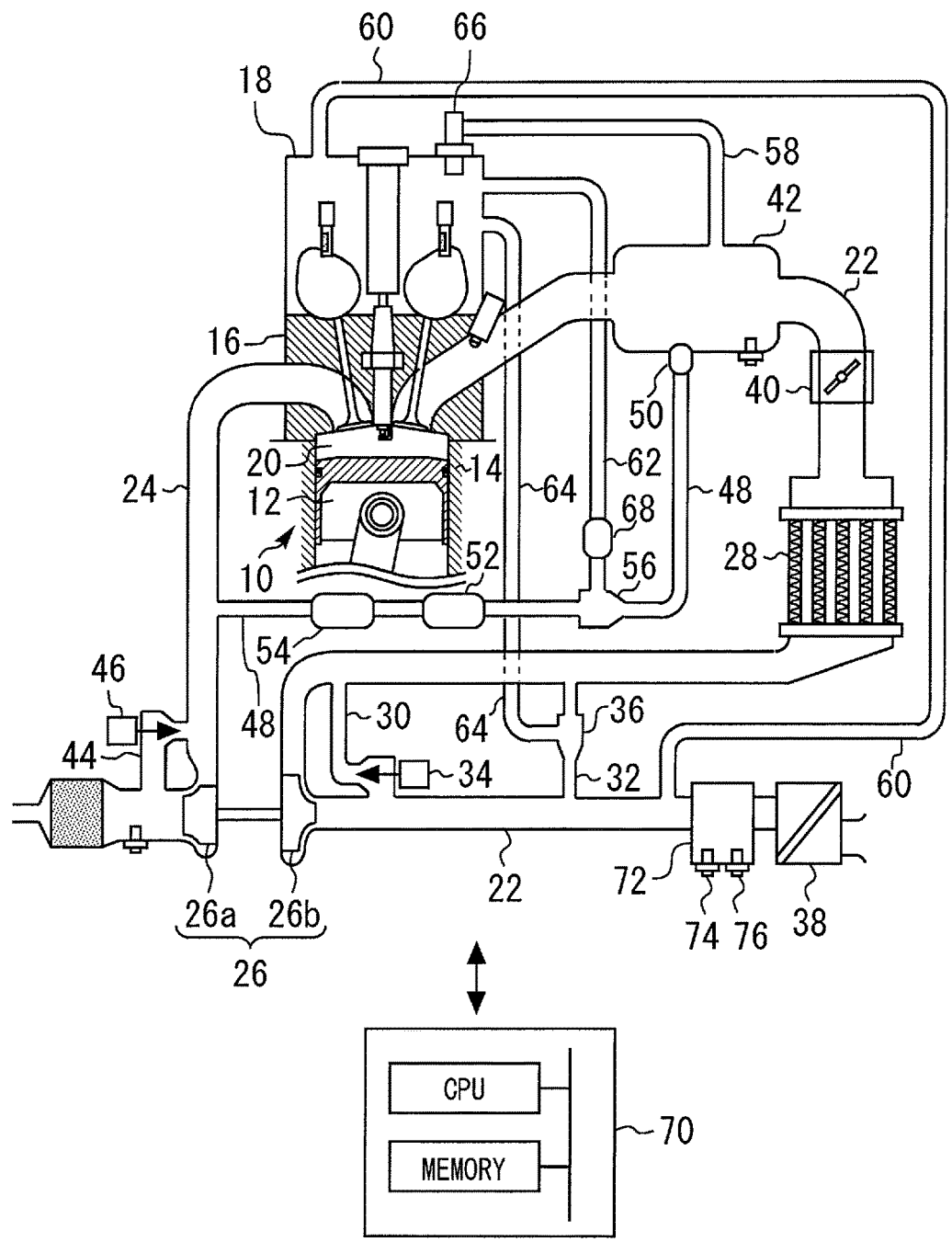
FIG. 1 is a diagram illustrating a system configuration of a first embodiment.

FIG. 1 is a diagram illustrating a system configuration of the first embodiment. As illustrated in FIG. 1, a system of the present embodiment includes an engine 10 as an internal combustion engine. The number of cylinders and disposition of the cylinders of the engine 10 are not specially limited. The engine 10 includes a cylinder block 14 having a piston 12 inside the cylinder block 14. A cylinder head 16 is assembled to an upper portion of the cylinder block 14. The cylinder head 16 is covered with a cylinder head cover 18. A space from a top surface of the piston 12 to the cylinder head 16 forms a combustion chamber 20. The cylinder head 16 includes an intake passage 22 and an exhaust passage 24 that communicate with the combustion chamber 20.

Further, the system of the present embodiment includes a turbocharger 26. The turbocharger 26 includes a turbine 26a provided in the exhaust passage 24, and a compressor 26b provided in the intake passage 22. The turbine 26a and the compressor 26b are connected to each other. At a time of an operation of the turbocharger 26, the compressor 26b is driven by the turbine 26a that rotates by receiving an exhaust pressure, and intake air is compressed and turbocharged by the compressor 26b.

In the intake passage 22, an intercooler 28 that cools the intake air that is turbocharged by the compressor 26b is provided. In the intake passage 22 at an upstream side from the intercooler 28, air bypass passages 30 and 32 that bypass the compressor 26b are provided. In the air bypass passage 30, an ABV (Air Bypass Valve) 34 is provided. By opening the ABV 34, an abrupt rise of turbocharging pressure is prevented. In the air bypass passage 32, an ejector 36 for introducing gas in a PCV passage 64 into the air bypass passage 32 is provided. Further, in the intake passage 22 at an upstream side of the compressor 26b, an air cleaner 38 is provided. In the intake passage 22 at a downstream side of the intercooler 28, an electronically controlled throttle valve 40 is provided. In the intake passage 22 at a downstream side of the throttle valve 40, a surge tank 42 is provided.

In the intake passage 22 that is at an upstream side of the compressor 26b and at a downstream side of the air cleaner 38, an air flow meter 72 for detecting an intake air amount is provided. A temperature sensor 74 to detect a temperature of intake air and a humidity sensor 76 to detect humidity of the intake air are incorporated inside the air flow meter 72.

Note that the temperature sensor 74 and the humidity sensor 76 may be configured separately from the air flow meter 72. Details of the humidity sensor 76 will be described later.

In the exhaust passage 24, an exhaust bypass passage 44 that bypasses the turbine 26a is provided. In the exhaust bypass passage 44, an electromagnetically driven type WGV (Waste Gate Valve) 46 is provided. Back pressure can be adjusted by opening the WGV 46, so that pump loss of the engine and an in-cylinder residual amount of exhaust gas are restrained.

Further, the system of the present embodiment is loaded with an EGR mechanism that recirculates exhaust gas to the intake passage 22 from the exhaust passage 24. The EGR mechanism includes an EGR passage 48 that connects the exhaust passage 24 at an upstream side of the turbine 26a, and the surge tank 42. On the EGR passage 48, an EGR valve 50 that adjusts an EGR gas amount, a water-cooled type EGR cooler 52, and an EGR catalyst 54 are provided. The EGR valve 50 is disposed in a position that is the nearest to the surge tank 42, and the EGR catalyst 54 is disposed in a position near the exhaust passage 24. Further, the EGR mechanism includes an ejector 56, between the EGR valve 50 and the EGR cooler 52. The ejector 56 is for introducing gas in a PCV passage 62 to the EGR passage 48.

Further, the system of the present embodiment includes a blow-by gas reducing mechanism that reduces blow-by gas. Blow-by gas refers to gas that flows into a crankcase from a gap between the piston 12 and a cylinder wall surface, and gas containing unburned fuel and oil mist. The blow-by gas reducing mechanism includes four kinds of PCV passages 58, 60, 62 and 64. The PCV passage 58 connects the cylinder head cover 18 and the surge tank 42. On the PCV passage 58, a PCV valve 66 is provided. The PCV passage 60 connects the cylinder head cover 18 and the intake passage 22, at an upstream side of the compressor 26b. The PCV passage 62 connects an intake port of the ejector 56 and the cylinder head cover 18. On the PCV passage 62, a PCV valve 68 is provided. The PCV passage 64 connects an intake port of the ejector 36 and the cylinder head cover 18.

In addition, the system of the present embodiment includes an ECU (Electronic Control Unit) 70. The ECU 70 includes at least an input/output interface, a memory and a CPU (a processor). The input/output interface is provided to take in sensor signals from various sensors that are attached to the internal combustion engine, and output operation signals to actuators included by the internal combustion engine. Sensors from which the ECU 70 takes in signals include various sensors that are necessary to control the engine 10, such as a throttle opening degree sensor to detect an opening degree of the throttle valve 40, and a temperature sensor to detect a cooling water temperature of the engine 10. Actuators to which the ECU outputs operation signals include various actuators such as the ABV 34, the throttle valve 40, the WGV 46 and the EGR valve 50. In the memory, various control programs for controlling the internal combustion engine, maps and the like are stored. The CPU (the processor) reads a control program or the like from the memory and executes the control program or the like, and generates an operation signal based on the sensor signal which is taken in.

1-2. Configuration of Humidity Sensor

Figure 2:
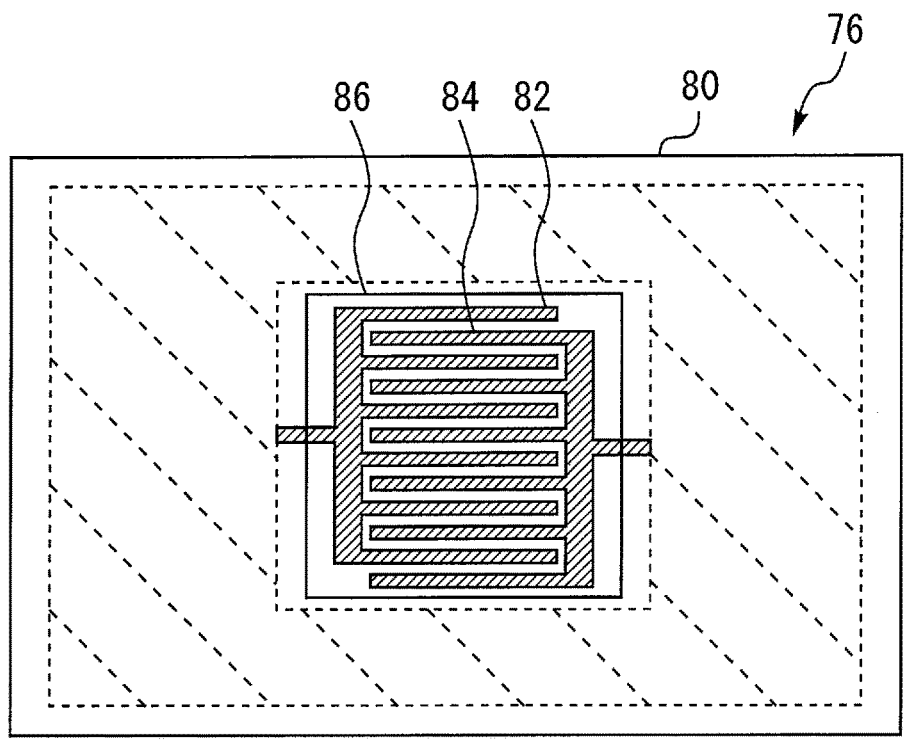
FIG. 2 is a view illustrating a schematic plan view of a humidity sensor used in a system of the first embodiment.

FIG. 2 is a view illustrating a schematic plan view of the humidity sensor 76 that is used in the system of the present embodiment. The humidity sensor 76 is an electrical capacitance type humidity sensor, and outputs a sensor signal corresponding to relative humidity. The humidity sensor 76 is configured mainly by a silicon substrate 80, detecting electrodes 82 and 84, and a humidity sensitive film 86. An insulator film is formed on the silicon substrate 80, and on the insulator film, the comb-shaped detecting electrodes 82 and 84 are disposed to face each other in such a manner as to be meshed with each other. Further, the humidity sensitive film 86 is a film in which an electric capacitance value changes in accordance with humidity, and is disposed in the silicon substrate 80 in such a manner as to cover the detecting electrodes 82 and 84. When water molecules enter into the film of the humidity sensitive film 86, a dielectric constant of the humidity sensitive film 86 changes greatly in accordance with an amount of the water which enters therein. Accordingly, the relative humidity around the sensor can be detected by detecting the change of the capacitance value between the detecting electrodes 82 and 84 as a sensor signal. Note that the humidity sensor 76 is not limited to an electrical capacitance type humidity sensor, but may be configured as another humidity sensor of an electric resistance type or the like.

1-3. Operation of System of First Embodiment

Figure 3:
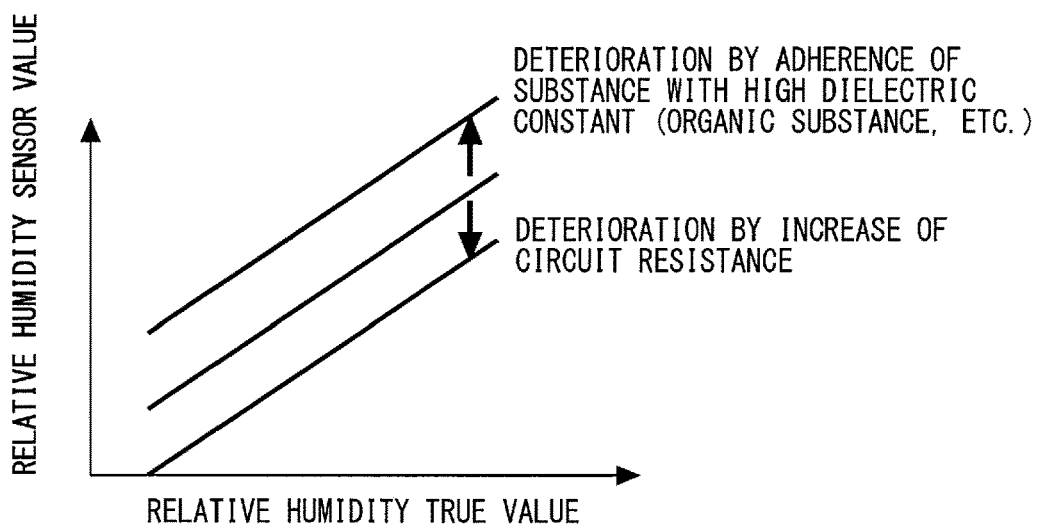
FIG. 3 is a diagram illustrating a relation between a sensor value of relative humidity and a true value of the relative humidity.

As described above, the humidity sensor 76 detects the relative humidity of external air by using the fact that the amount of water adsorbed by the humidity sensitive film 86 changes in accordance with the change of the humidity of the external air. Therefore, when the humidity sensitive film 86 adsorbs the matters other than water, for example, exhaust gas and organic substances in the atmosphere, an error is superimposed on the relative humidity which is detected. FIG. 3 is a diagram illustrating a relation between a sensor value of the relative humidity and a true value of the relative humidity. The sensor value of the relative humidity mentioned here refers to the relative humidity that is calculated from the sensor signal of the humidity sensor 76. As illustrated in FIG. 3, when deterioration caused by a substance with a high dielectric constant adhering to the humidity sensitive film 86 occurs, the sensor value corresponding to the true value of the relative humidity deviates to a high humidity side. Further, when a circuit of the humidity sensor 76 deteriorates and a circuit resistance increases, the sensor value corresponding to the true value of the relative humidity deviates to a low humidity side. In this way, a detection characteristic of the humidity sensor 76 is likely to change due to an ambient environment, aged deterioration or the like. Consequently, in order to keep a function of the humidity sensor 76, it is required to detect an abnormality that occurs to the humidity sensor 76 which is disposed in the intake passage 22 at an early stage.

However, the sensor value of the relative humidity also changes in accordance with a change of an intake air temperature. Consequently, even if the sensor values of the relative humidity under different intake air temperature conditions are simply compared, an abnormality of the humidity sensor 76 cannot be detected. Thus, in the system of the first embodiment, an abnormality of the humidity sensor 76 which is disposed in the intake passage 22 of the engine 10 is detected by using a detection method shown as follows.

1-3-1. Detection of Abnormality of Humidity Sensor in Warming-Up Period of Engine 10

Figure 4:
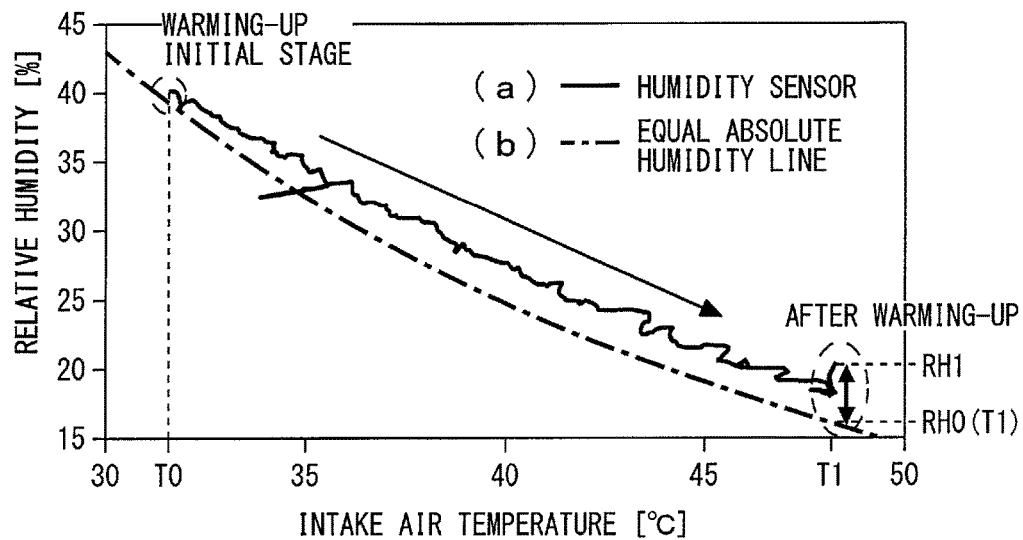
FIG. 4 is a diagram for explaining a method for detecting abnormality of the humidity sensor in a warming-up period of an engine.

FIG. 4 is a diagram for explaining a method for detecting an abnormality of the humidity sensor 76 in a warming-up period of the engine 10. A solid line illustrated by (a) in FIG. 4 represents a change of the relative humidity detected by the humidity sensor 76. Further, an alternate long and short dash line illustrated by (b) in FIG. 4 represents an equal absolute humidity line RH0 (T) of absolute humidity AH0 that is converted from a sensor signal S0 of the humidity sensor 76 in a time point of an initial stage of warming-up (a time point at which the intake air temperature is T0 in FIG. 4) of the engine 10. Note that the warming-up period mentioned here means a time period in which after cold start or the like of the engine 10, a temperature in an engine compartment increases with increase of a water temperature and an oil temperature.

When it is assumed that intake air with the equal absolute humidity continues to flow in the warming-up period of the engine 10, a theoretical value of the relative humidity transitions on the equal absolute humidity line with increase of the intake air temperature. Consequently, when relative humidity RH1 that is calculated from a sensor signal S1 of the humidity sensor 76 greatly deviates from relative humidity RH0 (T1) on the equal absolute humidity line at a time point (for example, a time point at which the intake air temperature in FIG. 4 is T1) after warming-up of the engine 10, for example, it can be determined that an abnormality occurs to the humidity sensor 76.

In this way, in the aforementioned abnormality detection method, the two sensor signals S0 and S1 under the different intake air temperature conditions are compared after the two sensor signals S0 and S1 are converted into the relative humidity RH0 (T1) and relative humidity RH1 with the intake air temperature conditions made equal. Thereby, an influence of an intake air temperature difference can be excluded from the two sensor signals under the different intake air temperature conditions, and therefore, it becomes possible to perform detection of an abnormality of the humidity sensor with high precision. Further, in the warming-up period of the engine 10, the intake air temperature greatly changes, and therefore, two sensor signals with the intake air temperature conditions greatly differing from each other can be easily detected.

In the aforementioned abnormality detection method, in detection of abnormality of the humidity sensor using the intake air temperatures T0 and T1, the relative humidities in the case of the intake air temperature being T1 are respectively calculated from these sensor signals and are compared. However, the intake air temperature conditions of both the sensor signals are not limited to the case in which the intake air temperatures are made equal to be T1. That is, the configuration may be adopted, in which relative humidities RH0 (Ta) and RH1 (Ta) or correlation values thereof in the case of the intake air temperature being a reference intake air temperature Ta (for example, T0<Ta<T1) are respectively calculated from the sensor signals in the case of the intake air temperatures being T0 and T1, and these values are compared.

Further, in the aforementioned abnormality detection method, determination of whether or not the relative humidity RH1 greatly deviates from the relative humidity RH0 (T1) can be performed according to whether or not a deviation degree of both the values is larger an a predetermined degree. As a value suitable for determining the deviation degree, a differential value between the relative humidity RH0 (T1) and the relative humidity RH1, and a ratio of the relative humidity RH0 (T1) and the relative humidity RH1 can be used, for example.

1-3-2. Detection of Abnormality of Humidity Sensor in Soak Period of Engine 10

Figure 5:
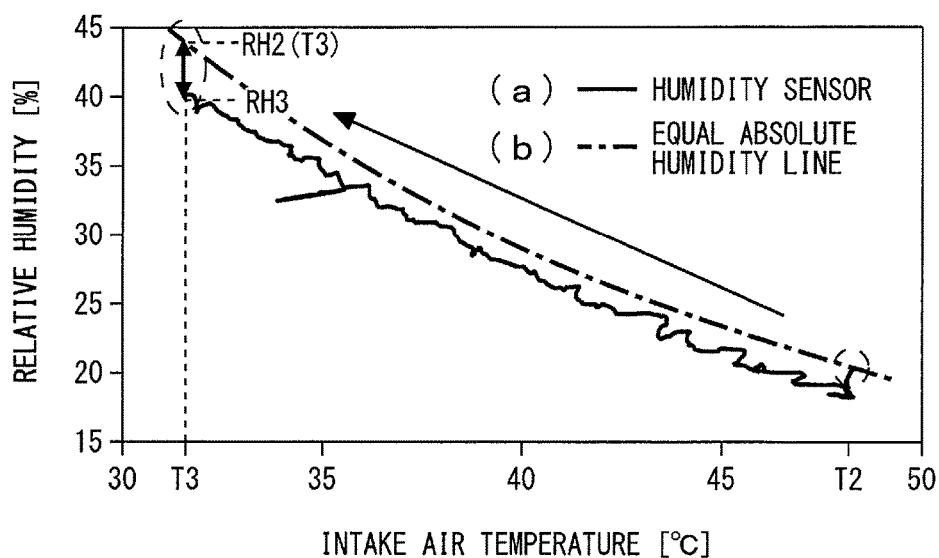
FIG. 5 is a diagram for explaining a method for detecting abnormality of the humidity sensor in a soak period after stop of the engine.

FIG. 5 is diagram for explaining a method for detecting abnormality of the humidity sensor 76 in a soak period after stopping of the engine 10. The soak period mentioned here means a period until start of a next time from stopping of the engine 10. Further, a solid line illustrated by (a) in FIG. 5 represents a change of a relative humidity detected by the humidity sensor 76. Further, an alternate long and short dash line illustrated by (b) in FIG. 5 represents an equal absolute humidity line RH2 (T) of an absolute humidity AH2 that is converted from a sensor signal S2 of the humidity sensor 76 at the time of stopping of the engine 10 (a time point at which the intake air temperature is T2 in FIG. 5). When it is assumed that humidity of the intake air in the intake passage 22 is constant in the soak period after the engine 10 is stopped, a theoretical value of the relative humidity transitions on the equal absolute humidity line with reduction of the intake air temperature. Consequently, it can be determined that an abnormality occurs to the humidity sensor 76 when relative humidity RH3 calculated from a sensor signal S3 of the humidity sensor 76 greatly deviates from relative humidity RH2 (T3) on the equal absolute humidity line at a time of end of the soak period, for example (a time point at which the intake air temperature is T3 in FIG. 5, for example).

In this way, the intake air temperature drops after stopping of the engine 10, and therefore, two sensor signals with different intake air temperature conditions can be easily detected. The situation in which the intake air temperature drops is not limited to the time after stopping of the engine 10. That is, for example, heat is not radiated by running wind during idling, and therefore an inside of an engine compartment sometimes has a relatively high temperature. When travelling is started from the state like this, reduction in the intake air temperature as illustrated in FIG. 5 occurs, and therefore detection of abnormality of the humidity sensor 76 may be executed by using the change of the intake air temperature at this time.

1-3-3. Detection of Abnormality of Humidity Sensor in Other Situations

Besides the warming-up period or the soak period of the engine 10 described above, detection of abnormality of the humidity sensor can be executed in any situation where the intake air temperature changes. The intake air temperature can be changed in a short time period by changing an air current from external air to the inlet of the intake passage 22. For example, if ON-OFF of a fan of a radiator is switched, the temperature in the engine compartment can be changed, and thereby, the intake air temperature can be changed. Further, in an engine including a grille which is openable and closable, the intake air temperature can be also changed by opening and closing the grille. Further, in an engine including a so-called hot air intake that introduces high-temperature intake air into the intake passage 22, the intake air temperature can be also changed by switching a change-over valve for switching introduction of the hot air intake. Furthermore, in an engine including a heat exchanger at a midpoint of the intake passage 22 or in the engine compartment, the intake air temperature can be also changed by operating the heat exchanger.

1-4. Configuration for Realizing Detection of Abnormality of Humidity Sensor

Figure 6:
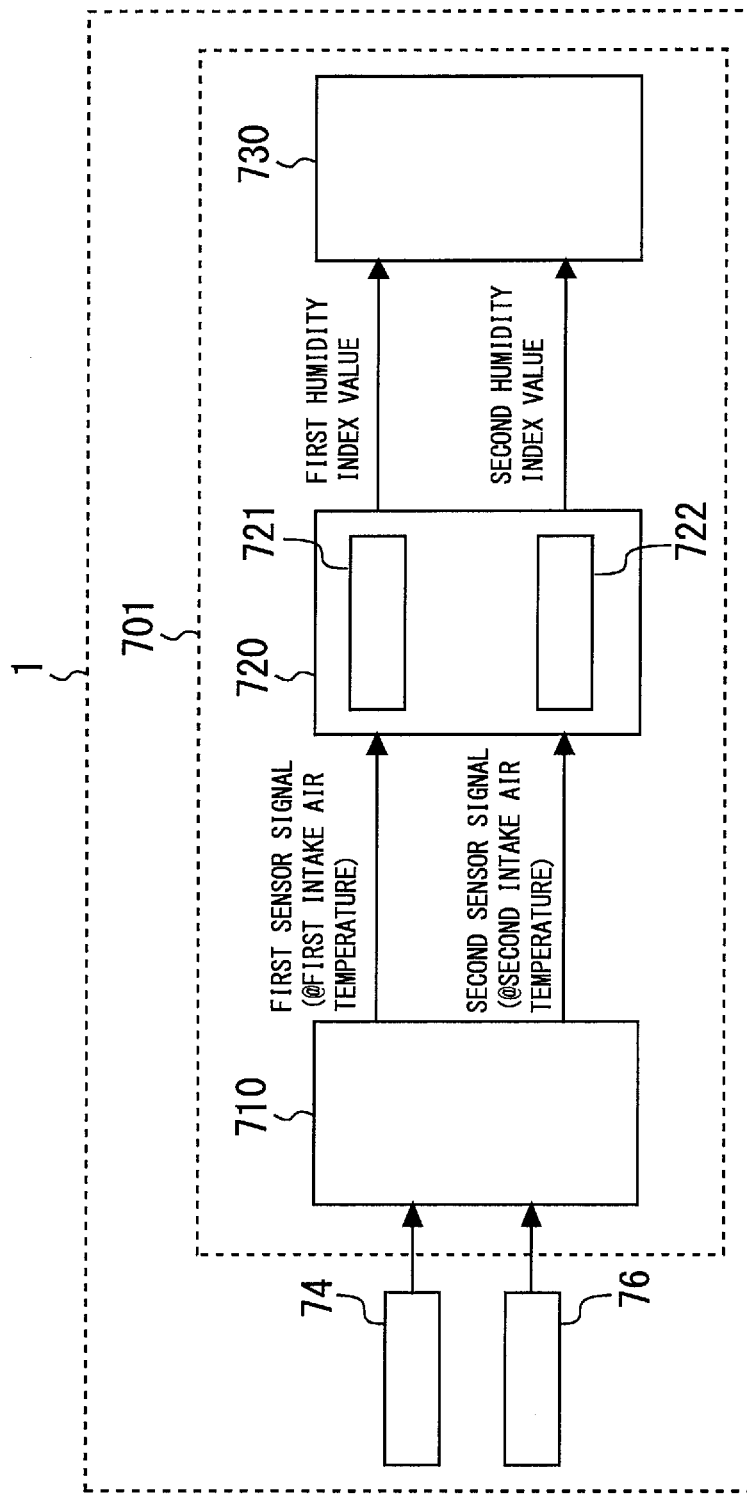
FIG. 6 is a functional block diagram illustrating a configuration of an abnormality detection device for the humidity sensor.

Next, a specific configuration for realizing detection of abnormality of the humidity sensor 76 will be described. Detection of abnormality of the humidity sensor 76 is realized by an abnormality detection device 1. FIG. 6 is a functional block diagram illustrating a configuration of the abnormality detection device 1 for the humidity sensor 76. The abnormality detection device 1 is configured by the humidity sensor 76, the temperature sensor 74 and a controller 701. The controller 701 is a part of a processing circuitry of the ECU 70, and is for realizing a function for detecting presence or absence of abnormality of the humidity sensor 76.

The controller 701 is configured by a sensor signal detection section 710, a calculation section 720 and an abnormality detection section 730. The sensor signal detection section 710 detects a first sensor signal that is a sensor signal of the humidity sensor 76 at a time of the intake air temperature being a first intake air temperature, and a second sensor signal that is a sensor signal of the humidity sensor 76 at a time of the intake air temperature changing from the first intake air temperature and reaching a second intake air temperature. The calculation section 720 receives input of the first sensor signal and the second sensor signal, and calculates a first humidity index value and a second humidity index value from which an influence by an intake air temperature difference is excluded, respectively from the sensor signals. In more detail, the calculation section 720 is configured by including a first calculation section 721 and a second calculation section 722. Subsequently, the first calculation section 721 receives input of the first sensor signal and calculates the first humidity index value, and the second calculation section 722 receives input of the second sensor signal and calculates the second humidity index value. The abnormality detection section 730 determines whether or not the humidity sensor 76 has abnormality according to whether or not a deviation degree of the first humidity index value and the second humidity index value which are inputted is large.

In the detection of abnormality of the humidity sensor 76 in the warming-up period of the engine 10 described above, the first intake air temperature in FIG. 6 corresponds to the intake air temperature T0, the second intake air temperature corresponds to the intake air temperature T1, the first sensor signal corresponds to the sensor signal S0, and the second sensor signal corresponds to the sensor signal S1. Further, the first humidity index value corresponds to the relative humidity RH0 (T1) in the case where the intake air temperature is changed to T1 in the absolute humidity AH0 calculated from the sensor signal S0, and the second humidity index value corresponds to the relative humidity RH1 calculated from the sensor signal S1. Further, when the sensor signals S0 and S1 are converted into relative humidities in the reference intake air temperature Ta, the first humidity index value corresponds to the relative humidity RH0 (Ta), and the second humidity index value corresponds to the relative humidity RH1 (Ta).

Further, in the detection of abnormality of the humidity sensor 76 in the soak period of the engine 10 described above, the first intake air temperature in FIG. 6 corresponds to the intake air temperature T2, the second intake air temperature corresponds to the intake air temperature T3, the first sensor signal corresponds to the sensor signal S2, the second sensor signal corresponds to the sensor signal S3. Further, the first humidity index value corresponds to the relative humidity RH2 (T3) in the case where the intake air temperature is changed to T3 in the absolute humidity AH2 calculated from the sensor signal S2, and the second humidity index value corresponds to the relative humidity RH3 calculated from the sensor signal S3.

Respective functions of the sensor signal detection section 710, the calculation section 720 and the abnormality detection section 730 in the controller 701 are realized by a processing circuitry. That is, the controller 701 includes the processing circuitry for detecting the first sensor signal which is the sensor signal in the case where the intake air temperature is the first intake air temperature, and the second sensor signal which is the sensor signal in the case where the intake air temperature is the second intake air temperature when the intake air temperature changes from the first intake air temperature to the second intake air temperature, calculating the values from which the influence of the temperature difference between the first intake air temperature and the second intake air temperature is excluded, from the first sensor signal and the second sensor signal which are detected, as the first humidity index value and the second humidity index value, and detecting presence or absence of abnormality of the humidity sensor according to whether or not the deviation degree of the first humidity index value and the second humidity index value which are calculated is larger than the predetermined degree. The processing circuitry is the CPU (Central Processing Unit, also referred to as a central processing device, a processing device, an arithmetic operation device, a microprocessor, a microcomputer, a processor, and a DSP) that executes the programs stored in the memory.

The functions of the sensor signal detection section 710, the calculation section 720 and the abnormality detection section 730 are realized by software, firmware, or a combination of software and firmware. The software and the firmware are described as programs, and are stored in the memory. The processing circuitry realizes the functions of the respective sections by reading the programs stored in the memory and executing the programs. That is, when the controller is realized by a processing circuitry, the controller includes the memory for storing the program by which a step of detecting the first sensor signal which is the sensor signal in the case where the intake air temperature is the first intake air temperature, and the second sensor signal which is the sensor signal in the case where the intake air temperature is the second intake air temperature, when the intake air temperature is changed from the first intake air temperature to the second intake air temperature, a step of calculating the values from which the influence of the temperature difference between the first intake air temperature and the second intake air temperature is excluded, as the first humidity index value and the second humidity index value, from the first sensor signal and the second sensor signal which are detected, and a step of detecting presence or absence of abnormality of the humidity sensor according to whether or not the deviation degree of the first humidity index value and the second humidity index value which are calculated is larger than the predetermined degree are executed as a result. Further, these programs can be said to cause a computer to execute procedures and methods of the sensor signal detection section 710, the calculation section 720 and the abnormality detection section 730. Here, a nonvolatile or volatile semiconductor memory such as a RAM, a ROM, a flash memory, an EPROM, or an EPPROM corresponds to the memory.

1-5. Execution Conditions of Detection of Abnormality of Humidity Sensor

In the detection of abnormality of the humidity sensor described above, it becomes possible to enhance detection precision by satisfying the following conditions.

Figure 7:
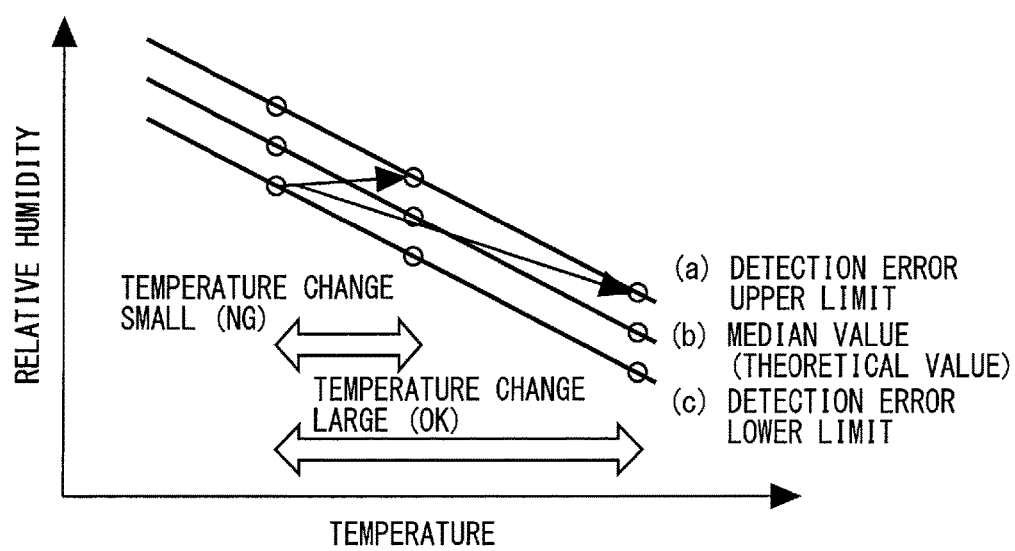
FIG. 7 is a diagram illustrating a change of the relative humidity to an intake air temperature.

1-5-1. Conditions for Securing Temperature Difference of Intake Air Temperatures FIG. 7 is a diagram illustrating a change of the relative humidity to the intake air temperature, (b) in FIG. 7 represents a median value (a theoretical value), (a) in FIG. 7 represents an upper limit value of a detection error, and (c) in FIG. 7 represents a lower limit value of the detection error, respectively. As illustrated in FIG. 7, when the temperature change of the intake air temperature is small, a large difference does not occur to the relative humidities which are detected, and therefore, a distinction cannot be made between abnormality of the humidity sensor and a detection error. Thus, the system of the first embodiment is configured to restrict abnormality determination for the humidity sensor when the temperature change of the intake air temperature is smaller than a predetermined value (an error span of the detected value, for example). According to the configuration like this, it becomes possible to determine abnormality of the humidity sensor and a detection error by clearly isolating the abnormality and the detection error from each other.

1-5-2. Conditions for External Air to Reach Humidity Sensor

When the engine 10 is started, absolute humidity of air in the intake passage 22 and the engine compartment before start is likely to differ from absolute humidity of external air at the time of the start. Thus, the system of the first embodiment is configured to restrict determination of abnormality of the humidity sensor in a period until the external air reaches the humidity sensor 76 after start of the engine 10. As the configuration like this, it is conceivable to restrict determination of abnormality of the humidity sensor until an integrated value of a volume of the intake air amount after start of the engine 10 exceeds an intake air capacity from the inlet of the intake passage 22 to the position where the humidity sensor 76 is disposed, for example. Further, when a configuration is such that air stays in the engine compartment, an air capacity of the engine compartment may be further taken into consideration. According to the configuration like this, an output signal after the external air reaches the humidity sensor can be used, and therefore determination of presence or absence of abnormality of the humidity sensor can be realized with high precision. Determination of whether the external air reaches the humidity sensor 76 may be set in accordance with a time period from the time of start of the engine 10.

1-5-3. Case where Gas Containing Fuel Components Reaches Humidity Sensor

The engine 10 of the first embodiment includes the EGR mechanism and the blow-by gas reducing mechanism. Consequently, under operation conditions in which the EGR gas and the blow-by gas are recirculated to the intake passage 22, it is assumed that these combustion gases reach the humidity sensor 76 by an influence of intake pulsation or the like. Thus, the system of the first embodiment is configured to restrict determination of abnormality of the humidity sensor under the conditions in which the gases containing combustion components such as EGR gas and blow-by gas reach the humidity sensor 76. According to the configuration like this, normal output signals of the humidity sensor 76 can be used, and therefore, determination of presence or absence of abnormality of the humidity sensor can be realized with high precision.

1-6. Specific Processing of System of First Embodiment

Figure 8:
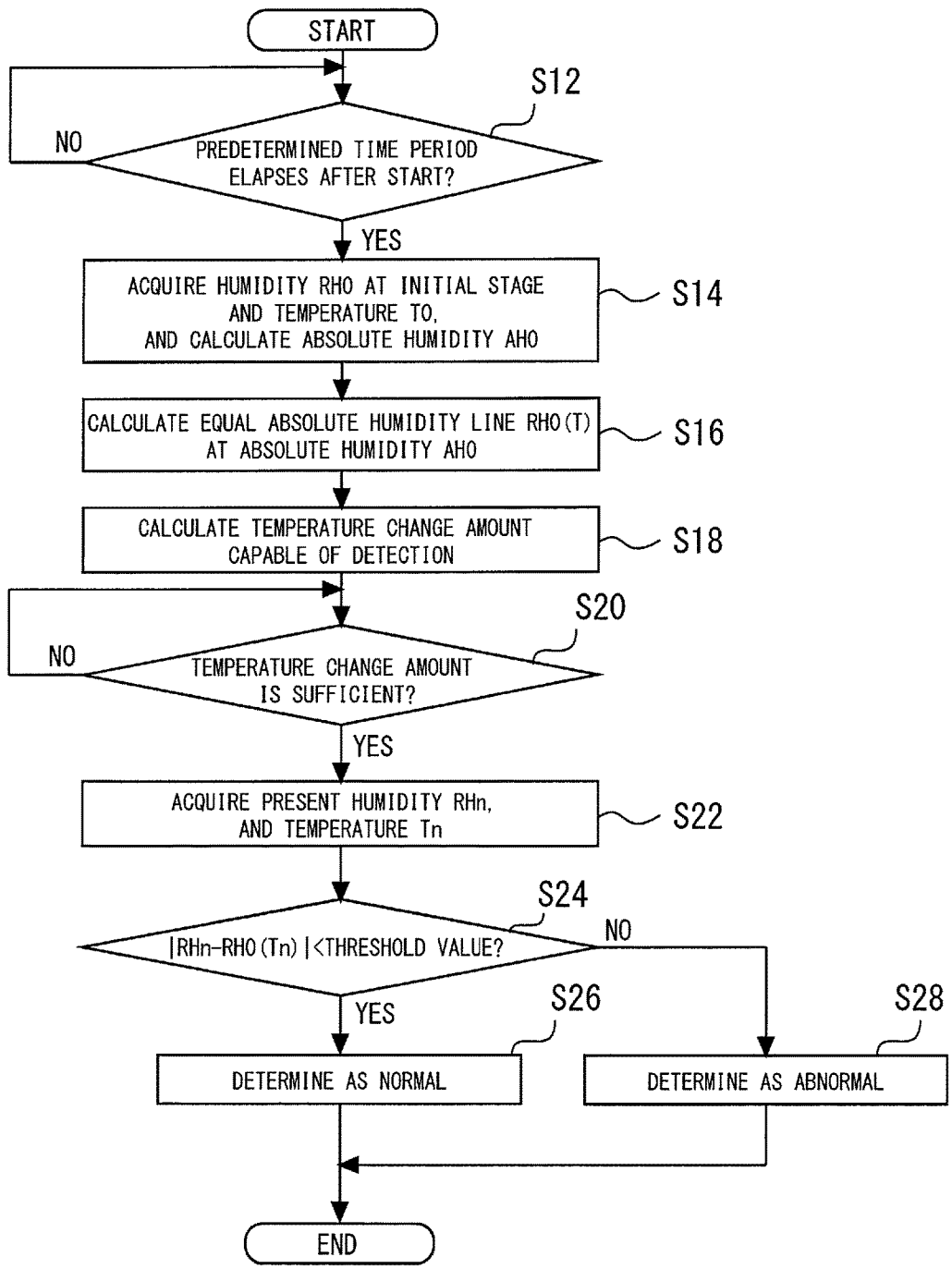
FIG. 8 is a flowchart of a routine that is executed by the system of the first embodiment.

Next, specific processing of determining presence or absence of abnormality of the humidity sensor that is executed in the system of the first embodiment will be described. FIG. 8 is a flowchart of a routine executed by the system of the first embodiment. The routine illustrated in FIG. 8 is a routine for determining presence or absence of abnormality of the humidity sensor in the warming-up period of the engine 10, and is executed by the ECU 70 at the time of start of the engine 10.

In the routine illustrated in FIG. 8, it is determined whether or not a predetermined time period elapses after start of the engine 10 (step S12). The predetermined time period is a time period required until the humidity sensor 76 issues a normal output signal, and is set from conditions or the like for the external air to reach the humidity sensor described above. When establishment of the condition of the present step is not recognized as a result, the processing of the present step is repeatedly executed, and when establishment of the condition of the present step is recognized, the flow goes to a next step.

In the next step, the relative humidity RH0 is calculated from the output signal of the humidity sensor 76, as the relative humidity at the initial stage of warming-up. Further, the intake air temperature T0 at the time of calculation of the relative humidity RH0 is calculated by using the temperature sensor 74. Furthermore, by using the intake air temperature T0, the absolute humidity AH0 corresponding to the relative humidity RH0 is calculated (step S14).

Next, the equal absolute humidity line RH0 (T) representing the change of the relative humidity in the equal absolute humidity is calculated (step S16). Next, the temperature change amount capable of detection is calculated (step S18). Here, more specifically, as the temperature change amount for determining whether or not the condition for securing the temperature difference of the intake air temperatures described above is satisfied, a value larger than the detection error span is calculated.

Next, it is determined whether or not the temperature change amount of the intake air temperature is sufficient (step S20). Here, more specifically, a present intake air temperature is detected, and it is determined whether or not the change amount from the intake air temperature T0 to the present intake air temperature is larger than the temperature change amount which is read in step S18 described above. When establishment of the present step is not recognized as a result, processing of the present step is repeatedly executed, and when establishment of the present step is recognized, the flow goes to a next step.

In the next step, as present relative humidity, relative humidity RHn is calculated from the output signal of the humidity sensor 76. Further, an intake air temperature Tn at the time of calculation of the relative humidity RHn is calculated by using the temperature sensor 74 (step S22).

Next, establishment of |RHn−RH0 (Tn)|<threshold value is determined (step S24). The relative humidity RH0 (Tn) is relative humidity at the time of the intake air temperature being Tn in the equal absolute humidity line RH0 (T) which is calculated in step S16 described above. Further, the threshold value is the threshold value for determining whether or not abnormality occurs to the humidity sensor 76, and a value that is set in advance is read. When establishment of |RHn−RH0 (Tn)|<threshold value is recognized as a result, the humidity sensor 76 is determined as normal (step S26). When establishment of |RHn−RH0 (Tn)|<threshold value is not recognized, the humidity sensor 76 is determined as abnormal (step S28). After the processing of step S26 or S28 described above is executed, the present routine is ended.

As described above, according to the system of the first embodiment, it becomes possible to determine whether or not abnormality occurs to the humidity sensor 76 provided in the intake passage 22, with high precision.

Incidentally, the routine illustrated in FIG. 8 can be applied to a routine for determining presence or absence of abnormality of the humidity sensor in the soak period of the engine 10. In this case, the routine illustrated in FIG. 8 can be executed at the time of stopping of the engine 10. However, the processing in step S12 is skipped since the processing in step S12 is the processing which relates to a time after the start of the engine 10.

In the system of the first embodiment described above, the abnormality detection device 1 corresponds to an abnormality detection device of a first embodiment of the present invention, and the humidity sensor 76 corresponds to a humidity sensor of the first embodiment of the present invention. The temperature sensor 74 corresponds to a temperature sensor of the first embodiment of the present invention, and the controller 701 corresponds to a processing circuitry of the first embodiment of the present invention. The sensor signal detection section 710 corresponds to the processing circuitry of the first embodiment of the present invention, the calculation section 720 corresponds to the processing circuitry of the first embodiment of the present invention. The abnormality detection section 730 corresponds to the processing circuitry of the first embodiment of the present invention.

Further, in the system of the first embodiment described above, the first calculation section 721 corresponds to the processing circuitry of a second embodiment of the present invention, and the second calculation section 722 corresponds to the processing circuitry of the second embodiment of the present invention.

Second Embodiment

Next, a second embodiment of the present embodiment of the present invention will be described with reference to the drawings. A system of the second embodiment is realized by causing the ECU 70 to execute a routine illustrated in FIG. 9 that will be described later, by using a hardware configuration similar to that of the first embodiment.

2-1. Operation of System of Second Embodiment

The system of the first embodiment is configured to convert the two sensor signals S0 and S1 with different intake air temperature conditions into the relative humidities RH0 (T1) and RH1 with the intake air temperature conditions made equal to each other and compare the relative humidities RH0 (T1) and RH1 thereafter. Here, absolute humidity is humidity that does not depend on a temperature, unlike relative humidity. Thus, in a system of the second embodiment, absolute humidities or correlation values thereof are respectively calculated from two sensor signals with different intake air temperature conditions, and presence or absence of sensor abnormality is determined according to whether or not these values greatly deviate from each other. As the condition in which the intake air temperature changes, the condition of the warming-up period of the engine 10 described above, the soak period after stopping of the engine 10 or the like can be used.

More specifically, in the warming-up period of the engine 10 in which the intake air temperature rises from T0 to T1, for example, the absolute humidity AH0 which is converted from the sensor signal S0 of the humidity sensor 76 at the time point at which the intake air temperature is T0, and the absolute humidity AH1 which is converted from the sensor signal S1 of the humidity sensor 76 at the time point at which the intake air temperature is T1 are calculated. When the absolute humidity AH0 greatly deviates from the absolute humidity AH1, it can be determined that abnormality occurs to the humidity sensor 76.

Detection of abnormality of the humidity sensor 76 in the system of the second embodiment is realized by the abnormality detection device 1 illustrated in FIG. 6 similar to the system of the first embodiment, in more detail, the humidity sensor 76, the temperature sensor 74 and the controller 701. In the detection of abnormality of the humidity sensor by comparison of the absolute humidities described above, the first intake air temperature in FIG. 6 corresponds to the intake air temperature T0, the second intake air temperature corresponds to the intake air temperature T1, the first sensor signal corresponds to the sensor signal S0, and the second sensor signal corresponds to the sensor signal S1. Further, the first humidity index value corresponds to the absolute humidity AH0 which is calculated from the sensor signal S0, and the second humidity index value corresponds to the absolute humidity AH1 which is calculated from the sensor signal S1.

2-2. Specific Processing of System of Second Embodiment

Figure 9:
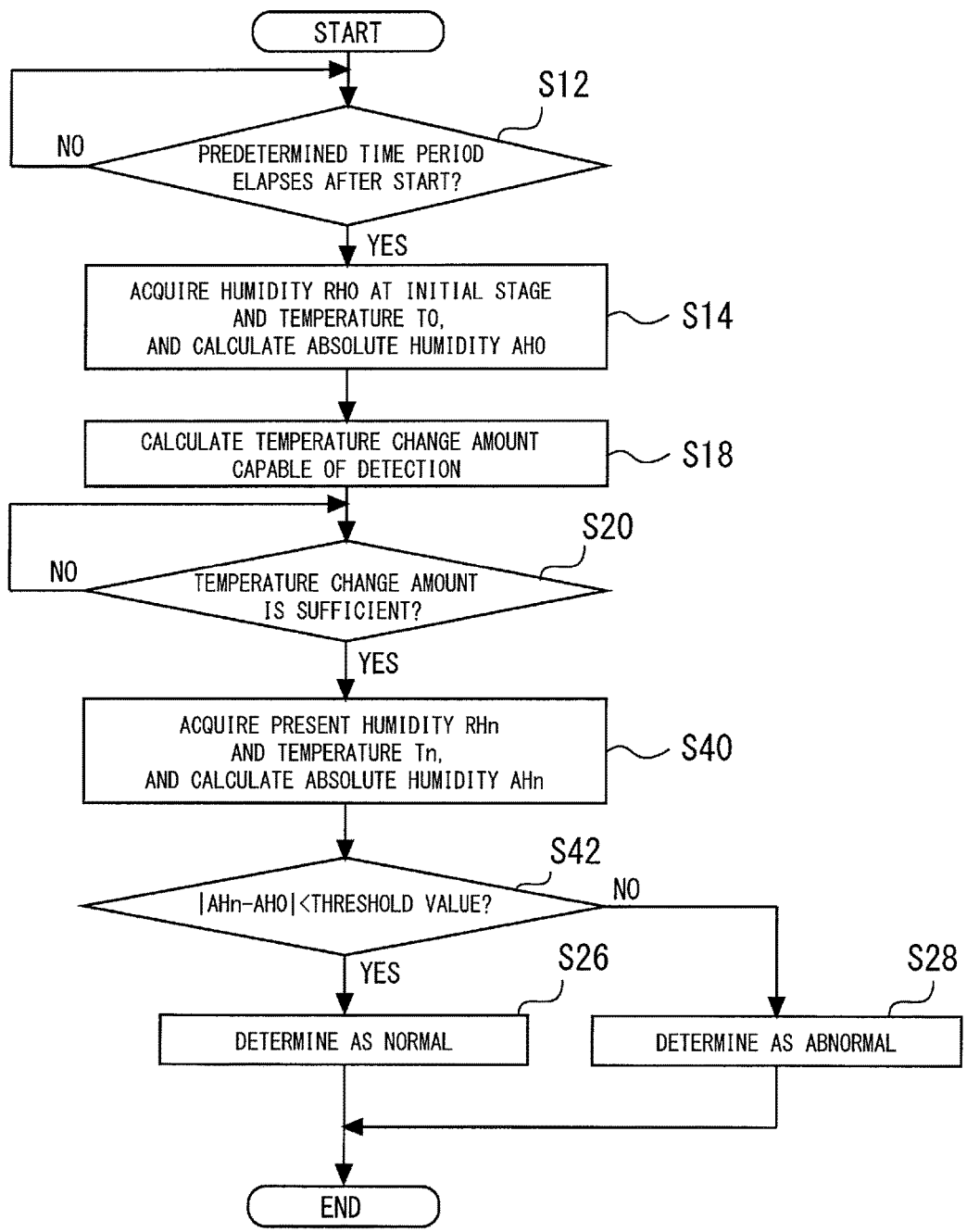
FIG. 9 is a flowchart of a routine that is executed by a system of a second embodiment.

Next, specific processing of the processing of determining presence or absence of abnormality of the humidity sensor that is executed in the system of the second embodiment will be described. FIG. 9 is a flowchart of a routine that is executed by the system of the second embodiment. The routine illustrated in FIG. 9 is a routine for determining presence or absence of abnormality of the humidity sensor in the warming-up period of the engine 10, and is executed by the ECU 70 at the time of start of the engine 10.

In steps S12, S14, S18 and S20 of the routine illustrated in FIG. 9, processing similar to the processing in steps S12, S14, S18 and S20 of the routine illustrated in FIG. 8 is executed. When establishment of step S20 is recognized, the flow goes to a next step.

In the next step, as the present relative humidity, the present relative humidity RHn is calculated from the output signal of the humidity sensor 76. Further, by using the temperature sensor 74, the intake air temperature Tn at the time of calculation of the relative humidity RHn is calculated. Further, by using the intake air temperature Tn, an absolute humidity AHn corresponding to the relative humidity RHn is calculated (step S40).

Next, establishment of |AHn−AH0|<threshold value is determined (step S42). The threshold value is the threshold value for determining whether or not abnormality occurs to the humidity sensor 76, and a value that is set in advance is read. When establishment of |AHn−AH0|<threshold value is recognized as a result, the humidity sensor 76 is determined as normal (step S26). When establishment of |AHn−AH0(Tn)|<threshold value is not recognized, the humidity sensor 76 is determined as abnormal (step S28). When the processing in step S26 or S28 described above is executed, the present routine is ended.

As described above, according to the system of the second embodiment, it becomes possible to determine whether or not abnormality occurs to the humidity sensor 76 which is provided in the intake passage 22, with high precision.

Incidentally, the routine illustrated in FIG. 9 can be applied to a routine for determining presence or absence of abnormality of the humidity sensor in the soak period of the engine 10, similarly to the routine illustrated in FIG. 8.

In the system of the second embodiment described above, the absolute humidity AH0 corresponds to first absolute humidity of a fifth embodiment of the present invention, and the absolute humidity AHn corresponds to second absolute humidity of the fifth embodiment of the present invention. The first calculation section 721 corresponds to a processing circuitry of the fifth embodiment of the present invention, and the second calculation section 722 corresponds to the processing circuitry of the fifth embodiment of the present invention.

What is claimed is:
1. An abnormality detection device for a humidity sensor, comprising:
    the humidity sensor that is disposed in an intake passage of an internal combustion engine, and outputs a sensor signal corresponding to relative humidity of intake air in the intake passage;
    a temperature sensor to detect an intake air temperature that is a temperature of the intake air; and
    a processing circuitry that is configured to detect presence or absence of abnormality of the humidity sensor based on the sensor signal and the intake air temperature,
    wherein the processing circuitry is configured to:
    detect a first sensor signal that is the sensor signal at a time of the intake air temperature being a first intake air temperature, and a second sensor signal that is the sensor signal at a time of the intake air temperature changing from the first intake air temperature and reaching a second intake air temperature,
    calculate a value correlated with the relative humidity at a time of the intake air temperature being a predetermined reference intake air temperature, as the first humidity index value, by using the first sensor signal,
    calculate a value correlated with the relative humidity at a time of the intake air temperature being the reference intake air temperature, as the second humidity index value, by using the second sensor signal, and
    detect presence or absence of abnormality of the humidity sensor according to whether or not a deviation degree of the first humidity index value and the second humidity index value is larger than a predetermined degree.

2. The abnormality detection device for a humidity sensor according to claim 1,
    wherein the reference intake air temperature is the second intake air temperature.

3. The abnormality detection device for a humidity sensor according to claim 1,
    wherein the reference intake air temperature is the first intake air temperature.

4. The abnormality detection device for a humidity sensor according to claim 1,
    wherein the processing circuitry is configured to detect the first sensor signal and the second sensor signal when the intake air temperature changes from the first intake air temperature to the second intake air temperature, in a warming-up period or a soak period of the internal combustion engine.

5. The abnormality detection device for a humidity sensor according to claim 1,
    wherein the processing circuitry is configured to prevent detection by the first sensor signal and the second sensor signal, until an integrated value of a volume of intake air that is taken into the intake passage after start of the internal combustion engine exceeds a capacity from an inlet to the humidity sensor in the intake passage, in a warming-up period of the internal combustion engine.

6. The abnormality detection device for a humidity sensor according to claim 1,
    wherein the processing circuitry is configured to set the second intake air temperature so that the temperature difference becomes a predetermined temperature difference or more.

7. The abnormality detection device for a humidity sensor according to claim 1,
    wherein the processing circuitry is configured to prevent detection by the first sensor signal and the second sensor signal when gas containing fuel components flows in the intake passage of the internal combustion engine.

8. An abnormality detection device for a humidity sensor, comprising:

the humidity sensor that is disposed in an intake passage of an internal combustion engine, and outputs a sensor signal corresponding to relative humidity of intake air in the intake passage, a temperature sensor to detect an intake air temperature that is a temperature of the intake air; and a processing circuitry that is configured to detect presence or absence of abnormality of the humidity sensor based on the sensor signal and the intake air temperature, wherein the processing circuitry is configured to:

detect a first sensor signal that is the sensor signal at a time of the intake air temperature being a first intake air temperature, and a second sensor signal that is the sensor signal at a time of the intake air temperature changing from the first intake air temperature and reaching a second intake air temperature, calculate values from which an influence of a temperature difference between the first intake air temperature and the second intake air temperature is excluded, from the first sensor signal and the second sensor signal, as a first humidity index value and a second humidity index value, respectively, and detect presence or absence of abnormality of the humidity sensor according to whether or not a deviation degree of the first humidity index value and the second humidity index value is larger than a predetermined degree, wherein the processing circuitry is configured to prevent detection by the first sensor signal and the second sensor signal, until an integrated value of a volume of intake air that is taken into the intake passage after start of the internal combustion engine exceeds a capacity from an inlet to the humidity sensor in the intake passage, in a warming-up period of the internal combustion engine.

9. The abnormality detection device for a humidity sensor according to claim 8, wherein the processing circuitry is configured to:

calculate a value correlated with first absolute humidity that is absolute humidity at the time of the intake air temperature being the first intake air temperature, as the first humidity index value, by using the first sensor signal, and calculate a value correlated with second absolute humidity that is absolute humidity at a time of the intake air temperature being the second intake air temperature, as the second humidity index value, by using the second sensor signal.

10. The abnormality detection device for a humidity sensor according to claim 8, wherein the processing circuitry is configured to detect the first sensor signal and the second sensor signal when the intake air temperature changes from the first intake air temperature to the second intake air temperature, in a warming-up period or a soak period of the internal combustion engine.

11. The abnormality detection device for a humidity sensor according to claim 8, wherein the processing circuitry is configured to set the second intake air temperature so that the temperature difference becomes a predetermined temperature difference or more.

12. The abnormality detection device for a humidity sensor according to claim 8, wherein the processing circuitry is configured to prevent detection by the first sensor signal and the second sensor signal when gas containing fuel components flows in the intake passage of the internal combustion engine.

* * * * *